United States Patent
Shinmen et al.

(10) Patent No.: US 11,896,918 B2
(45) Date of Patent: Feb. 13, 2024

(54) COMPOSITION SUPPLY METHOD, COMPOSITION, SUPPLY DEVICE, AND COMPOSITION FILLING METHOD

(71) Applicant: CENTRAL GLASS COMPANY, LIMITED, Ube (JP)

(72) Inventors: Masutaka Shinmen, Ube (JP); Azusa Miyake, Ube (JP); Masayoshi Imachi, Ube (JP); Ryusei Sezaki, Ube (JP)

(73) Assignee: Central Glass Company, Limited, Yamaguchi (JP)

( * ) Notice: Subject to any disclaimer, the term of this patent is extended or adjusted under 35 U.S.C. 154(b) by 408 days.

(21) Appl. No.: 17/235,590

(22) Filed: Apr. 20, 2021

(65) Prior Publication Data

US 2021/0331085 A1    Oct. 28, 2021

(30) Foreign Application Priority Data

Apr. 24, 2020    (JP) .................. 2020-077601

(51) Int. Cl.
| | | |
|---|---|---|
| *B01B 1/00* | (2006.01) | |
| *B67C 3/00* | (2006.01) | |
| *C07C 211/08* | (2006.01) | |
| *F17C 7/04* | (2006.01) | |
| *B01J 7/00* | (2006.01) | |
| *B01J 19/00* | (2006.01) | |
| *B01J 4/00* | (2006.01) | |

(52) U.S. Cl.
CPC .................. *B01B 1/005* (2013.01); *B01J 7/00* (2013.01); *B01J 19/0013* (2013.01); *B67C 3/007* (2013.01); *C07C 211/08* (2013.01); *F17C 7/04* (2013.01); *B01J 4/00* (2013.01); *B01J 2219/00051* (2013.01); *F17C 2221/03* (2013.01)

(58) Field of Classification Search
CPC ....... C07C 211/08; C07C 211/07; F17C 3/007
See application file for complete search history.

(56) References Cited

U.S. PATENT DOCUMENTS

| | | |
|---|---|---|
| 2017/0008039 A1 | 1/2017 | Weinberger et al. |
| 2019/0055469 A1 | 2/2019 | Hyakutake |
| 2019/0292660 A1 | 9/2019 | Aoki et al. |

FOREIGN PATENT DOCUMENTS

| | | |
|---|---|---|
| JP | 9-309796 | 12/1997 |
| JP | 2006-183863 | 7/2006 |
| JP | 2006-265162 | 10/2006 |
| JP | 2010-138164 | 6/2010 |
| JP | 2018-123878 | 8/2018 |
| WO | 2017/159544 | 9/2017 |
| WO | 2018/016375 | 1/2018 |

*Primary Examiner* — Jafar F Parsa
(74) *Attorney, Agent, or Firm* — Hamre, Schumann, Mueller & Larson, P.C.

(57) ABSTRACT

The present disclosure provides a method for stably supplying a highly pure n-butylamine gas having a constant composition. The present disclosure is a composition supply method including: a filling step of filling a container with a composition containing n-butylamine in an amount of 99.5% by volume or more and isobutylamine in an amount of 0.001% by volume or more and 0.5% by volume or less; a warming step of warming the container filled with the composition to 50° C. or higher; and a gas supply step of supplying a gas containing n-butylamine and isobutylamine from the warmed container to a predetermined device.

15 Claims, No Drawings

COMPOSITION SUPPLY METHOD, COMPOSITION, SUPPLY DEVICE, AND COMPOSITION FILLING METHOD

CROSS-REFERENCE TO RELATED APPLICATIONS

The present application claims priority under 35 U.S.C. § 119 to Japanese Patent Application No. 2020-077601 filed on Apr. 24, 2020, the contents of which are incorporated herein by reference in their entirety.

BACKGROUND OF THE INVENTION

Field of the Invention

The present disclosure relates to a method for supplying a gas composition containing n-butylamine and isobutylamine, a composition containing n-butylamine and isobutylamine, a gas composition supply device, and a filling method for a composition containing n-butylamine and isobutylamine.

Description of Related Art n-Butylamine, which is an organic amine, is used in pharmaceutical manufacturing processes and semiconductor device manufacturing processes. In such applications, n-butylamine is preferably supplied in the form of gas.

Raw materials used in the pharmaceutical manufacturing processes or semiconductor device manufacturing processes are preferably highly pure and not likely to have a compositional change. However, in supply of n-butylamine in the form of gas from a container filled with n-butylamine, the n-butylamine concentration unfortunately changes between at the beginning and end of use of the container.

CITATION LIST

Patent Literature

Patent Literature 1: WO 2017/159544

BRIEF SUMMARY OF THE INVENTION

A method for supplying a gasified azeotropic composition containing a fluorinated saturated hydrocarbon and an amine compound has been reported as a method for maintaining the composition of the gas constant during supply thereof (see WO 2017/159544, for example). However, an azeotropic composition is difficult to use here because a gas containing n-butylamine does not have a constant n-butylamine concentration during its supply and n-butylamine and impurities contained therein are not capable of forming an azeotrope.

In view of the above problem, the present disclosure aims to provide a method for stably supplying a highly pure n-butylamine gas having a constant composition.

The present inventors made intensive studies to find out the following: n-butyl amine contains isobutylamine as an impurity at a variable concentration, which prevents supply of an n-butylamine gas having a constant composition. The present inventors further found out that reduction in the amount of isobutylamine in the composition for filling enables supply of a constant-composition gas containing n-butylamine and isobutylamine. Thus, the present disclosure was completed.

The present inventors also found out that warming of a container filled with a composition containing n-butylamine and isobutylamine to a predetermined temperature or higher to supply a gas containing n-butylamine and isobutylamine to a predetermined device enables supply of highly pure n-butylamine in a constant composition. Thus, the present disclosure was completed.

Specifically, a composition supply method of the present disclosure includes: a filling step of filling a container with a composition containing n-butylamine in an amount of 99.5% by volume or more and isobutylamine in an amount of 0.001% by volume or more and 0.5% by volume or less; a warming step of warming the container filled with the composition to 50° C. or higher; and a gas supply step of supplying a gas containing n-butylamine and isobutylamine from the warmed container to a predetermined device.

According to the composition supply method of the present disclosure, n-butylamine can be supplied in the form of gas having a constant composition.

A composition of the present disclosure contains n-butylamine in an amount of 99.5% by volume or more and isobutylamine in an amount of 0.001% by volume or more and 0.5% by volume or less.

When the composition of the present disclosure is supplied by the above supply method, n-butylamine in the form of gas having a constant composition can be supplied.

A supply device of the present disclosure includes multiple containers filled with the composition. The containers are warmed to 50° C. or higher. The supply device is capable of supplying an n-butylamine composition in the form of gas.

The supply device of the present disclosure allows use of one container filled with the composition alone or use of multiple containers filled with the composition together, further contributing to supply of n-butylamine in the form of gas having a further constant composition.

A composition filling method of the present disclosure includes: a filling step of filling a container with a composition containing n-butylamine in an amount of 99.5% by volume or more and isobutylamine in an amount of 0.001% by volume or more and 0.5% by volume or less; a warming step of warming the container filled with the composition to 50° C. or higher; and a discharging step of discharging 5% by mass or more of the composition in the container in the form of gas from the warmed container.

The use of a filled container obtained by the composition filling method of the present disclosure enables supply of n-butylamine in the form of gas having a constant composition.

According to the composition supply method of the present disclosure, a variation in the isobutylamine concentration is reduced to supply highly pure n-butylamine in a constant composition.

DETAILED DESCRIPTION OF THE INVENTION

The present disclosure is described in detail below. The following description of structural elements provides exemplary embodiments of the present disclosure. The present disclosure is not limited to these specific embodiments. Various modifications can be made within the scope of the gist.

The composition supply method of the present disclosure includes: a filling step of filling a container with a composition containing n-butylamine in an amount of 99.5% by volume or more and isobutylamine in an amount of 0.001% by volume or more and 0.5% by volume or less; a warming step of warming the container filled with the composition to 50° C. or higher; and a gas supply step of supplying a gas containing n-butylamine and isobutylamine from the warmed container to a predetermined device.

In the case where the container is filled with the composition containing n-butylamine and isobutylamine and then the composition is discharged from the container after warming the container to gasify n-butylamine and isobutylamine, a gas composition at an initial stage of the discharge contains a greater proportion of isobutylamine than the composition filled in the container. According to the composition supply method of the present disclosure, the proportion of isobutylamine in the composition for filling is lowered to reduce change in the isobutylamine concentration.

The isobutylamine concentration of the gas composition is particularly high from the start of discharge up until the time when 5% by mass of the composition is discharged from the container. In the composition supply method of the present disclosure, it is preferred that the gas composition containing a high proportion of isobutylamine is discharged in advance to lower the isobutylamine concentration of the gas composition before supply of the gas composition to a predetermined device.

First, the filling step of filling a container with a composition is described.

In the present disclosure, a composition to fill a container may be prepared by any method that provides a composition containing n-butylamine in an amount of 99.5% by volume or more and isobutylamine in an amount of 0.001% by volume or more and 0.5% by volume or less. For example, the composition may be obtained during synthesis of n-butylamine by a conventionally known method, obtained by adding isobutylamine to n-butylamine, or obtained by distillation of a mixture containing n-butylamine in an amount of less than 99.5% by volume and isobutylamine in an amount of more than 0.5% by volume.

In the present disclosure, the composition to fill a container preferably has a smaller isobutylamine content. Accordingly, the composition is suitably prepared by distillation of a mixture containing n-butylamine and isobutylamine before the filling step.

The term "distillation" refers to vaporization and condensation of a liquid mixture containing multiple liquids different in boiling point for separation and purification of the components. Herein, n-butylamine and isobutylamine have close boiling points but are not azeotropic, which enables preparation of a composition having a lower isobutylamine concentration by distillation. Thus, the distillation enables preparation of the composition.

The composition to fill a container contains preferably n-butylamine in an amount of 99.5% by volume or more and isobutylamine in an amount of 0.001% by volume or more and 0.2% by volume or less, more preferably n-butylamine in an amount of 99.9% by volume or more and isobutylamine in an amount of 0.001% by volume or more and 0.05% by volume or less, still more preferably n-butylamine in an amount of 99.95% by volume or more and isobutylamine in an amount of 0.001% by volume or more and 0.01% by volume or less, particularly preferably n-butylamine in an amount of 99.99% by volume or more and isobutylamine in an amount of 0.001% by volume or more and 0.005% by volume or less. The composition having a composition within the above range enables supply of highly pure n-butylamine gas having compositional stability with less change in the isobutylamine concentration.

The composition may contain impurities different from n-butylamine or isobutylamine, and examples of the impurities include moisture, inert gas, oxygen, nitrogen, carbon monoxide, and carbon dioxide.

The composition may fill any container that can store liquid components including n-butylamine and isobutylamine. Examples of such a container include stainless steel (SUS) containers, manganese steel containers, nickel steel containers, and chromium molybdenum steel containers.

Next, the warming step is described.

In this step, the container filled with the composition is warmed to 50° C. or higher. At a temperature lower than 50° C., n-butylamine and isobutylamine are not sufficiently gasified and n-butylamine in the form of gas is hardly supplied. The container is warmed to preferably 60° C. to 90° C., more preferably 70° C. to 75° C.

The container is preferably warmed for 30 to 120 minutes.

The container may be warmed by any method known to a person skilled in the art, such as covering the container with a heating mantle or covering the container with a jacket in which a heating medium such as warm water or steam is circulated.

In the composition supply method of the present disclosure, a discharging step is preferably carried out before the gas supply step. The discharging step is described in the following.

In this step, 5% by mass or more of the composition in the container is preferably discharged from the warmed container in the form of gas. Upon discharge of a gas containing n-butylamine and isobutylamine from the container, the isobutylamine concentration of the gas at an initial stage of the discharge is higher than the isobutylamine concentration of the composition in the container. The isobutylamine concentration of the gas composition is particularly high from the start of the discharge up until the time when 5% by mass of the composition is discharged.

The isobutylamine concentration of the gas discharged from the container is gradually lowered. When the amount of the discharged gas reaches an amount corresponding to 10% by mass or more of the composition, the isobutylamine concentration of the gas becomes lower than the isobutylamine concentration of the composition at the start of discharge.

Accordingly, in the composition supply method of the present disclosure, the gas is preferably just discharged, not supplied to a device or the like, from the start of the discharge up until the time when the gas in an amount corresponding to 5% by mass or more, preferably 10% by mass or more of the composition is discharged. The discharged gas can be recovered. The discharged gas can be purified by re-distillation or the like to be used again. The upper limit of the amount of the gas discharged in the discharging step is not limited. For ensuring the quantity of the gas to be supplied in the supplying step, the upper limit is preferably 20% by mass or less, more preferably 15% by mass or less.

After the warming step or after the discharging step, the gas supply step of supplying a gas containing n-butylamine and isobutylamine to a predetermined device from the warmed container is carried out.

A gas containing n-butylamine and isobutylamine may be supplied to a predetermined device by, for example, directly introducing a gas of the composition from the container to the predetermined device through a supply part provided to connect the container filled with the composition and the predetermined device.

In the composition supply method of the present disclosure, for example, a gas can be supplied from a cylinder cabinet that stores the container filled with the composition in a casing and is capable of warming the container.

In the gas supply step, the composition of the supplied gas changes with the supply thereof. The isobutylamine concentration of the gas is lowered as more gas is supplied.

In a preferred embodiment of the present disclosure, the gas supplied in the gas supply step contains n-butylamine in an amount of 99.5% by volume or more and isobutylamine in an amount of 0.001% by volume or more and 0.5% by volume or less.

In a more preferred embodiment of the present disclosure, the gas supplied in the gas supply step contains n-butylamine in an amount of 99.5% by volume or more and isobutylamine in an amount of 0.001% by volume or more and 0.2% by volume or less.

In a still more preferred embodiment of the present disclosure, the gas supplied in the gas supply step contains n-butylamine in an amount of 99.9% by volume or more and isobutylamine in an amount of 0.001% by volume or more and 0.05% by volume or less.

In a particularly preferred embodiment of the present disclosure, the gas supplied in the gas supply step contains n-butylamine in an amount of 99.95% by volume or more and isobutylamine in an amount of 0.001% by volume or more and 0.01% by volume or less.

In a most preferred embodiment of the present disclosure, the gas supplied in the gas supply step contains n-butylamine in an amount of 99.99% by volume or more and isobutylamine in an amount of 0.001% by volume or more and 0.005% by volume or less.

The gas supply step can be carried out using multiple containers. Specifically, multiple containers are subjected to the filling step, the warming step, and the discharging step prior to the gas supply step. Then, the gas supply step is started for a first container and subsequently started for a second container after 50% by mass or more of the composition in the first container is used.

In other words, the gas supply step is started for any one of the multiple containers and subsequently started for another container after 50% by mass or more of the composition in the first container is used, which allows supply of a gas simultaneously from the multiple containers.

The isobutylamine concentration of the gas supplied from the container after 50% by mass or more of the composition filled therein is used is lower than the isobutylamine concentration of the gas supplied from the container after completion of the discharging step (e.g., usage of 5 to 10% by mass). Accordingly, supply of a gas from multiple containers different in usage of the composition filled therein enables supply of a gas having a relatively high isobutylamine concentration and a gas having a relatively low isobutylamine concentration in admixture.

The timing for starting the gas supply step for another container is herein set to after 50% by mass or more of the composition in the first container is used. Yet, the usage of the composition for the timing may be 60% by mass or more, or 70% by mass or more.

In the case of the gas supply step using multiple containers, the amounts of gas supplied from the multiple containers may be the same or different. In the case where two containers are used, for example, the gas supply ratio (volume ratio) may be 1:9 to 9:1. In that case, the proportion of the gas supplied from another container may be set small at the initial stage and gradually increased with use of the composition in the another container.

Upon supply of a gas to a predetermined device, gases (gas compositions) different in composition from multiple channels may be directly supplied to the predetermined device. Preferably, the gas compositions different in composition are mixed to be supplied through one channel to the predetermined device.

As a method of mixing multiple gas compositions, for example, a relay container of a predetermined volume may be provided in the middle of the gas supply channel from the containers to a predetermined device. The multiple gas compositions are once introduced into the relay container, and the gas composition mixture is supplied from the relay container to the predetermined device through a single channel. Alternatively, a container for mixing the gas compositions different in composition may be provided in the predetermined device.

Examples of the predetermined device include a device for producing pharmaceuticals or semiconductor devices.

The present disclosure also encompasses a composition for use in the composition supply method, the composition containing n-butylamine in an amount of 99.5% by volume or more and isobutylamine in an amount of 0.001% by volume or more and 0.5% by volume or less.

The composition of the present disclosure contains preferably n-butylamine in an amount of 99.5% by volume or more and isobutylamine in an amount of 0.001% by volume or more and 0.2% by volume or less, more preferably n-butylamine in an amount of 99.9% by volume or more and isobutylamine in an amount of 0.001% by volume or more and 0.05% by volume or less, still more preferably n-butylamine in an amount of 99.95% by volume or more and isobutylamine in an amount of 0.001% by volume or more and 0.01% by volume or less, particularly preferably n-butylamine in an amount of 99.99% by volume or more and isobutylamine in an amount of 0.001% by volume or more and 0.005% by volume or less.

The composition can be prepared, for example, by distillation of a mixture containing n-butylamine and isobutylamine, as described above.

The present disclosure also encompasses a supply device including multiple containers filled with the composition. The containers are warmed to 50° C. or higher. The supply device is capable of supplying an n-butylamine composition in the form of gas.

The supply device of the present disclosure may have any configuration that enables supply of an n-butylamine composition from any one container and supply of an n-butylamine composition simultaneously from multiple containers.

The supply device of the present disclosure may further include a supply part connecting the multiple containers filled with the composition and a predetermined device and a warming part for warming the containers. The supply device may include multiple supply parts connecting the containers and the predetermined device or a single supply part connecting the multiple containers and the predetermined device.

Specifically, the supply device may be configured to allow, upon supply of a gas composition to a predetermined device, supply of a gas composition from one container to the predetermined device through a single channel or supply of gas compositions different in composition from multiple containers directly to the predetermined device through multiple channels.

Yet, it is preferred that the supply device has a configuration that allows, upon supply of gas compositions different in composition from multiple containers to a predetermined device through multiple channels, mixing of the gas compositions different in composition in a relay container provided in the middle of the gas supply channels to supply a gas composition mixture to the predetermined device through a single channel, or that the predetermined device includes a container for mixing the gas compositions different in composition.

The supply device of the present disclosure is preferably a supply device used in the composition supply method of the present disclosure described above.

Examples of the container and the relay container include stainless steel (SUS) containers, manganese steel containers, nickel steel containers, and chromium molybdenum steel containers. Examples of a gas pipe for supplying a gas composition include stainless steel (SUS) gas pipes, manganese steel gas pipes, nickel steel gas pipes, chromium molybdenum steel gas pipes, and aluminum alloy gas pipes.

The container is warmed to 50° C. or higher. Examples of the warming method include placing the container in a heating mantle or covering the container with a jacket in which a heating medium such as warm water or steam is circulated.

The flow rate of the gas composition varies depending on the configuration of the predetermined device and is not limited. The flow rate of the gas composition can be controlled using, for example, a mass flow controller.

Examples of the supply device of the present disclosure include a cylinder cabinet including: a casing storing a container filled with an n-butylamine composition, a warming part capable of warming the container, a supply part connecting the container and a predetermined device, and a flow rate controller controlling the supply amount of a gas composition.

The present disclosure also encompasses a composition filling method including: a filling step of filling a container with a composition containing n-butylamine in an amount of 99.5% by volume or more and isobutylamine in an amount of 0.001% by volume or more and 0.5% by volume or less; a warming step of warming the container filled with the composition to 50° C. or higher; and a discharging step of discharging 5% by mass or more of the composition in the container in the form of gas from the warmed container.

The filling step, warming step, and discharging step in the composition filling method of the present disclosure may be carried out as in the filling step, warming step, and discharging step of the composition supply method of the present disclosure. Preferred embodiments thereof are the same as those for the composition supply method of the present disclosure.

Since initial 5% by mass or more of the composition in the container filled with the composition, i.e., the filled container, obtained in the composition filling method of the present disclosure has been discharged, the amount of the composition in the filled container is less than 95% by mass of the composition having filled the container in the filling step. Owing to the discharge of 5% by mass or more of the filing composition, the isobutylamine concentration in the filled container is lower than the isobutylamine concentration of the composition upon filling.

EXAMPLES

The following examples more specifically disclose embodiments of the present disclosure. The present disclosure is not intended to be limited only to these examples.

Example 1

A 1-L SUS container was filled with 0.7 kg of an n-butylamine composition obtained by distillation of a mixture containing n-butylamine and isobutylamine. According to the composition analysis (at 20° C.), the liquid phase of the filling n-butylamine composition contained n-butylamine in an amount of 99.933% by volume and isobutylamine in an amount of 0.044% by volume. The container was warmed to 70° C. Sixty minutes later, purging was started and the composition analysis of the gaseous phase was conducted. The gaseous phase was cooled to be collected and the composition thereof was analyzed using a gas chromatograph analyzer (GC-2014, available from Shimadzu Corporation, detector: FID). The gaseous phase contained n-butylamine in an amount of 99.933% by volume and isobutylamine in an amount of 0.044% by volume.

Then, purging was performed at a flow rate of 1000 sccm. After purging of 5% by mass of the filled amount in the container (usage: 5% by mass) was confirmed, the composition of the gaseous phase was analyzed. The results showed that the gaseous phase contained n-butylamine in an amount of 99.933% by volume and isobutylamine in an amount of 0.050% by volume. Purging was then continued. During the usage range from 10% by mass to 90% by mass, the composition of the purged gas was analyzed for every purging in an amount of 10% by mass. Table 1 shows the results. In Table 1, BA denotes n-butylamine and IBA denotes isobutylamine.

TABLE 1

| Usage | Temperature | BA (vol %) | IBA (vol %) | Others |
| --- | --- | --- | --- | --- |
| Full (liquid phase) | 20° C. | 99.933 | 0.044 | 0.023 |
| 1 mass % | 70° C. | 99.927 | 0.056 | 0.017 |
| 5 mass % | 70° C. | 99.933 | 0.050 | 0.017 |
| 10 mass % | 70° C. | 99.938 | 0.045 | 0.017 |
| 20 mass % | 70° C. | 99.944 | 0.039 | 0.017 |
| 30 mass % | 70° C. | 99.949 | 0.034 | 0.017 |
| 40 mass % | 70° C. | 99.952 | 0.030 | 0.018 |
| 50 mass % | 70° C. | 99.955 | 0.027 | 0.018 |
| 60 mass % | 70° C. | 99.956 | 0.026 | 0.018 |
| 70 mass % | 70° C. | 99.956 | 0.025 | 0.019 |
| 80 mass % | 70° C. | 99.957 | 0.024 | 0.019 |
| 90 mass % | 70° C. | 99.957 | 0.023 | 0.020 |

From the start of purging (usage: 1% by mass) to the usage of 5% by mass, the isobutylamine concentration of the gas was higher than the isobutylamine concentration of the liquid phase upon filling. When the usage reached 10% by mass, the isobutylamine concentration of the gas was almost the same as the isobutylamine concentration of the liquid phase upon filling. During the usage range from 20% by mass to 90% by mass, the isobutylamine concentration was gradually lowered. During the usage range from 10% by mass to 90% by mass, the maximum value and minimum value of the isobutylamine concentration were respectively 0.045% by volume and 0.023% by volume. The difference between the maximum value and the minimum value was 0.022% by volume.

Example 2

Two 1-L SUS containers (container 1 and container 2) were each filled with 0.7 kg of an n-butylamine composition obtained by distillation of a mixture containing n-butylamine and isobutylamine. According to the composition analysis (at 20° C.), the gaseous phases of the n-butylamine compositions filling the container 1 and the container 2 each contained n-butylamine in an amount of 99.933% by volume and isobutylamine in an amount of 0.044% by volume. The container 1 and the container 2 were both warmed to 70° C.

Sixty minutes later, purging was started and the gas was discharged to set the usage of the container 1 to 70% by mass and the usage of the container 2 to 10% by mass.

Then, the container 1 and the container 2 were subjected to purging at the same flow rate (1000 sccm). After mixing of the gases, the composition thereof was analyzed. Table 2 shows the results. After the usage of the container 1 reached 100% by mass, no gas was supplied from the container 1 and the gas composition from the container 2 alone was analyzed.

TABLE 2

| Container 1 (usage) | Container 2 (usage) | Supply ratio (Container 1:Container 2) | IBA (vol %) |
|---|---|---|---|
| 70 mass % | 10 mass % | 5:5 | 0.0350 |
| 80 mass % | 20 mass % | 5:5 | 0.0315 |
| 90 mass % | 30 mass % | 5:5 | 0.0288 |
| 100 mass % | 40 mass % | 0:10 | 0.0300 |
| — | 50 mass % | 0:10 | 0.0270 |
| — | 60 mass % | 0:10 | 0.0260 |
| — | 70 mass % | 0:10 | 0.0250 |

As shown in Table 2, in Example 2, the maximum value and minimum value of the isobutylamine concentration was respectively 0.0350% by volume and 0.0250% by volume. The difference between the maximum value and the minimum value was 0.0100% by volume. Thus, gas supply from two containers different in usage can reduce variation in isobutylamine concentration of the gas.

Example 3

The purging was performed as in Example 2, except that the ratio between the supply from the container 1 and the supply from the container 2 was changed as shown in Table 3, and the composition analysis was performed. Table 3 shows the results.

TABLE 3

| Container 1 (usage) | Container 2 (usage) | Supply ratio (Container 1:Container 2) | IBA (vol %) |
|---|---|---|---|
| 70 mass % | 10 mass % | 8:2 | 0.0290 |
| 80 mass % | 12.5 mass % | 5:5 | 0.0335 |
| 90 mass % | 22.5 mass % | 3.6:6.4 | 0.0320 |
| 100 mass % | 40 mass % | 0:10 | 0.0300 |
| — | 50 mass % | 0:10 | 0.0270 |
| — | 60 mass % | 0:10 | 0.0260 |
| — | 70 mass % | 0:10 | 0.0250 |

As shown in Table 3, the maximum value and minimum value of the isobutylamine concentration in Example 3 were respectively 0.0335% by volume and 0.0250% by volume. The difference between the maximum value and the minimum value was 0.0085% by volume. Gradual change in the ratio of the supplies from two containers different in usage can further reduce variation in isobutylamine concentration of the gas.

What is claimed is:

1. A composition supply method comprising:
   a filling step of filling a container with a composition containing n-butylamine in an amount of 99.5% by volume or more and isobutylamine in an amount of 0.001% by volume or more and 0.5% by volume or less;
   a warming step of warming the container filled with the composition to 50° C. or higher; and
   a gas supply step of supplying a gas containing n-butylamine and isobutylamine from the warmed container to a predetermined device.

2. The composition supply method according to claim 1, further comprising, prior to the gas supply step, a discharging step of discharging 5% by mass or more of the composition in the container in the form of gas from the warmed container.

3. The composition supply method according to claim 1, further comprising, prior to the gas supply step, a discharging step of discharging 10% by mass or more of the composition in the container in the form of gas from the warmed container.

4. The composition supply method according to claim 1, wherein the warming step involves warming the container to 60° C. to 90° C.

5. The composition supply method according to claim 1, wherein the warming step involves warming the container to 70° C. to 75° C.

6. The composition supply method according to claim 1, wherein the composition is prepared by distillation of a mixture containing n-butylamine and isobutylamine prior to the filling step.

7. The composition supply method according to claim 1, wherein the composition contains n-butylamine in an amount of 99.5% by volume or more and isobutylamine in an amount of 0.001% by volume or more and 0.2% by volume or less.

8. The composition supply method according to claim 1, wherein the composition contains n-butylamine in an amount of 99.9% by volume or more and isobutylamine in an amount of 0.001% by volume or more and 0.05% by volume or less.

9. The composition supply method according to claim 2, wherein the filling step, the heating step, and the discharging step are carried out for multiple containers prior to the gas supply step, and the gas supply step is started for a first container and subsequently started for a second container after 50% by mass or more of the composition in the first container is used.

10. The composition supply method according to claim 9, wherein the amount of the composition in the form of gas supplied from the first container is different from the amount of the composition in the form of gas supplied from the second container in the gas supply step.

11. A composition comprising n-butylamine in an amount of 99.5% by volume or more and isobutylamine in an amount of 0.001% by volume or more and 0.5% by volume or less.

12. The composition according to claim 11, comprising n-butylamine in an amount of 99.5% by volume or more and isobutylamine in an amount of 0.001% by volume or more and 0.2% by volume or less.

13. The composition according to claim 11, comprising n-butylamine in an amount of 99.9% by volume or more and isobutylamine in an amount of 0.001% by volume or more and 0.05% by volume or less.

14. A supply device comprising multiple containers filled with a composition comprising n-butylamine in an amount of 99.5% by volume or more and isobutylamine in an amount of 0.001% by volume or more and 0.5% by volume or less, wherein when the containers are warmed to 50° C. or higher, the supply device is configured to supply an n-butylamine composition in the form of gas.

15. A composition filling method comprising:
   a filling step of filling a container with a composition containing n-butylamine in an amount of 99.5% by volume or more and isobutylamine in an amount of 0.001% by volume or more and 0.5% by volume or less;

a warming step of warming the container filled with the composition to 50° C. or higher; and a discharging step of discharging 5% by mass or more of the composition in the container in the form of gas from the warmed container.

* * * * *